United States Patent
Lozano Teruel et al.

(10) Patent No.: US 10,272,120 B2
(45) Date of Patent: Apr. 30, 2019

(54) SYNERGISTIC COMPOSITION COMPRISING PROPOLIS AND CARNOSIC ACID FOR USE IN THE PREVENTION AND TREATMENT OF CANDIDIASIS

(71) Applicant: VITALGAIA ESPANA, S.L, Murica (ES)

(72) Inventors: Jose Antonio Lozano Teruel, Murica (ES); Juan Carlos Arguelles Ordonez, Murica (ES); Alejandra Arguelles Prieto, Murica (ES); Ruth Sanchez-Fresneda Pinto, Murica (ES); Jose Pedro Guirao Abad, Murica (ES)

(73) Assignee: VITALGAIA ESPANA, S.L, Murcia (ES)

( * ) Notice: Subject to any disclaimer, the term of this patent is extended or adjusted under 35 U.S.C. 154(b) by 21 days.

(21) Appl. No.: 15/546,879

(22) PCT Filed: Feb. 4, 2015

(86) PCT No.: PCT/IB2015/000140
§ 371 (c)(1),
(2) Date: Jul. 27, 2017

(87) PCT Pub. No.: WO2016/124957
PCT Pub. Date: Aug. 11, 2016

(65) Prior Publication Data
US 2018/0021389 A1 Jan. 25, 2018

(51) Int. Cl.
| | | |
|---|---|---|
| *A61K 9/10* | (2006.01) | |
| *A61K 35/644* | (2015.01) | |
| *A61K 31/05* | (2006.01) | |
| *A61K 31/192* | (2006.01) | |
| *A61K 31/352* | (2006.01) | |
| *A23L 21/20* | (2016.01) | |
| *A23K 20/111* | (2016.01) | |
| *A23L 33/10* | (2016.01) | |
| *A23K 20/10* | (2016.01) | |
| *A23L 33/105* | (2016.01) | |
| *A23G 3/36* | (2006.01) | |
| *A23G 3/48* | (2006.01) | |
| *A23G 4/06* | (2006.01) | |
| *A23G 4/12* | (2006.01) | |
| *A61K 47/10* | (2017.01) | |
| *A61K 9/06* | (2006.01) | |
| *A61K 9/12* | (2006.01) | |
| *A61K 9/20* | (2006.01) | |
| *A61K 9/48* | (2006.01) | |

(52) U.S. Cl.
CPC ............ *A61K 35/644* (2013.01); *A23G 3/364* (2013.01); *A23G 3/48* (2013.01); *A23G 4/068* (2013.01); *A23G 4/12* (2013.01); *A23K 20/10* (2016.05); *A23K 20/111* (2016.05); *A23L 21/20* (2016.08); *A23L 33/10* (2016.08); *A23L 33/105* (2016.08); *A61K 31/05* (2013.01); *A61K 31/192* (2013.01); *A61K 31/352* (2013.01); *A23V 2002/00* (2013.01); *A61K 9/06* (2013.01); *A61K 9/10* (2013.01); *A61K 9/12* (2013.01); *A61K 9/2054* (2013.01); *A61K 9/4866* (2013.01); *A61K 47/10* (2013.01)

(58) Field of Classification Search
None
See application file for complete search history.

(56) References Cited

FOREIGN PATENT DOCUMENTS

| DE | 20207155 U1 * | 9/2002 | ........... A61K 36/185 |
|---|---|---|---|
| EP | 2808009 A1 | 12/2014 | |

OTHER PUBLICATIONS

Firas Abbas Al-Bayati: Antimicrobial activity of carnosic acid isolated from Rosmarinus officinalis; XP002741565; Jan. 1, 2011.
Patricia Alves De Castro, et al; Identification of the cell targets important for propolis-induced cell death in Candida albicans; Fungal Genetics and Biology; vol. 60; Jul. 13, 2003; XP028772268; pp. 74-86.
International Search Report dated Jul. 14, 2015 for PCT/IB2015/000140.
Written Opinion dated Jul. 14, 2015 for PCT/IB2015/000140.

* cited by examiner

*Primary Examiner* — Nannette Holloman
(74) *Attorney, Agent, or Firm* — Lucas & Mercanti, LLP

(57) ABSTRACT

Synergistic composition comprising propolis and carnosic acid for use in the prevention and treatment of candidiasis. The invention relates to a synergistic composition comprising propolis that comprises polyphenols at a concentration between 70 and 90% by weight of propolis and carnosic acid, for use in the prevention and treatment of candidiasis in humans and/or animals. The invention also relates to a synergistic pharmaceutical and/or veterinary composition and a synergistic food product.

20 Claims, 12 Drawing Sheets

SYNERGISTIC COMPOSITION COMPRISING PROPOLIS AND CARNOSIC ACID FOR USE IN THE PREVENTION AND TREATMENT OF CANDIDIASIS

CROSS REFERENCE TO RELATED APPLICATION

This Application is a 371 of PCT/IB2015/000140 filed on Feb. 4, 2015, which is incorporated herein by reference.

TECHNICAL FIELD

The technical field of the invention is the treatment of infections by microorganisms of the genus *Candida* in humans and animals. In particular, the present invention relates to a synergistic composition comprising propolis and carnosic acid for use in the prevention and treatment of candidiasis.

BACKGROUND OF THE INVENTION

The genus *Candida*, especially *Candida albicans*, is currently the most prevalent etiologic agent of systemic mycoses. However, since 1980, several epidemiological analyses have documented the growing impact of outbreaks caused by "non-*C. albicans*" species in the bloodstream; it is the case of *C. glabrata* in the US and *C. parapsilosis* and *C. tropicalis* in Europe, Canada and Latin America. Although considered less virulent than *C. albicans* these species of *Candida* have great clinical impact, especially affecting immunity compromised patients or those weakened by invasive surgery and prolonged treatment with antibiotics.

The species of *Candida*, which have been the subject of general research, and so far have failed to be combated effectively by naturally occurring compounds, are those listed below:
Candida parapsilopsis
Candida glabrata
Candida tropicalis
Candida krusei
Candida dubliniensis
Candida guillermondi
Candida lusitaniae

*C. albicans* being the most virulent and therefore the scientific community should focus more efforts on it to combat it effectively.

C. albicans

The yeast *Candida albicans* is defined as an imperfect fungus whose habitat is obligatorily associated with humans and other warm-blooded animals. Taxonomic studies of sequence homology and analysis of physiological and phenotypic similarities situate *C. albicans* within the group of ascomycete yeasts with no real sexual cycle. The genus *Candida* is primarily characterised in that it includes species with unpigmented colony morphology, reference to which is made under the species name of "albicans", being this absence of pigmentation made visible by means of caretenoid compounds. They are able to use carbohydrates through fermentation and grow in the temperature range of mesophilic microorganisms (25-42° C.). As the main hydrocarbon reserve, it accumulates glycogen and also synthesises trehalose, whose content varies depending on the growth phase.

However, the biological activity of *C. albicans* differs substantially in two essential aspects from the rest of the ascosporogenic saprophytic yeasts, exemplified through *Saccharomyces cerevisiae* by:

Its required association with homeothermic animals, as mentioned.

Its status as an imperfect fungus, lacking real natural sexual cycle. *C. albicans* is a permanent diploid and therefore is obliged to divide by asexual reproduction. This property carries an additional difficulty for genetic analysis, although in recent years considerable progress has been made in the development of new molecular tools.

Clinical Significance

*Candida albicans* is considered the most prevalent opportunistic pathogenic microorganism in the human species. It is a common fungus of the commensal flora in healthy individuals, causing both superficial and systemic infections in the oral mucosa, digestive system or vaginal tract. As a commensal organism, it lives in harmless equilibrium with its host. However, *C. albicans* becomes a very virulent pathogen when the immune system is lowered or is severely weakened, being very frequent the occurrence of invasive candidiasis in AIDS sufferers, diabetics, patients undergoing intensive surgery or transplant recipients, infants, the elderly and persons subject to antitumor antibiotic therapy or prolonged treatment.

Superficial and Systemic Candidiasis

Infections caused by various species of the genus *Candida* are named candidiasis. Although *C. albicans* is the most important, other common species such as *C. tropicalis, C. glabrata, C. krusei, C. dubliensis* and *C. lusitaniae*, are often isolated in clinical samples as highly virulent pathogens. The candidiasis can be of two types:

Superficial: Affecting primarily the skin and mucous membranes of the oral and vaginal cavities, sometimes extending to the nails and scalp Systemic: In this case, the cells of the pathogen proliferate extensively in the blood, affecting one or more vital organs and generally causing symptoms of septicemia (or candidemia).

The clinical incidence of this opportunistic fungus has increased in recent years with an increasing segment of the population having altered immune defences, and it is equally a major health problem of hospital-associated type infections.

Virulence Factors

Interactions between parasite and host are an essential pathogenicity factor. Thus, factors of virulence in *C. albicans* are considered as all the genetic and physiological characteristics relating to its ability to cause infection to the host, to resist antifungal therapy, or to damage the cells and tissues that it invades. Among the virulence factors of *C. albicans* stand out:

The hydrophobicity of the cell surface.
The synthesis of molecules involved in the host adhesion.
The formation of biofilms on prostheses or catheters.
The secretion of hydrolytic enzymes.
The mycelium-yeast dimorphic change and other phenotypic changes ("switching").

Antifungal Susceptibility

The treatment with conventional specific antifungals, such as azoles (ketoconazole or fluconazole) and amphotericin B have only proven useful in reducing (oropharyngeal, oesophageal or vaginal) mucocutaneous candidiasis and cryptococcosis in patients with AIDS. However, in the case of generalised candidiasis, routine administration of these drugs is not recommended because its absorption is poor, its effectiveness limited and it tends to favour the emergence of resistant strains.

The search for new antifungal substances endowed with both potent pharmacological action and selective high toxicity is an urgent clinical need, due to the dramatic increase in systemic and hospital-associated fungal infections. Epidemiological data show how the incidence of total hospital-associated infections has increased 10 times (candidiasis represents 17% on the total) in the past five years, and numerous cases of affected immunocompromised patients have been reported.

The main research efforts are aimed at finding new antifungal targets. The study of the cell wall has been given great attention and thus the clinical use of a new antifungal agent of the Echinocandins family, which act as specific inhibitors of glucan synthase, involved in the synthesis of β-(1,3)-glucan, the main component of the cell wall, has already been approved. Early evidence shows that the application of caspofungin to invasive candidiasis achieves a similar efficacy to the treatments with fluconazole or liposomal amphotericin B, but with a much higher tolerability.

Although active ingredients from natural extracts such as: *Cuminum cyminum, Salvadora persica, Syngonanthus nitens, Tulbaghia alliacea, Alternaria alternata, Trichoderma* spp., *Arthrinium arundinis, Selaginella tamariscina, Glycyrrhizine* and *Citrus bergamia*, have been studied in various scientific experiments, none of them have proved to be an effective antifungal agent against *Candida* infections.

In the research world and the application thereof to existing pathologies in the matter at hand, there are some gaps in implementation and effectiveness.

In this sense, we could say that in the present state we find that each condition is sectorally and individually treated, so that the active ingredient used to try to combat pyorrhoea is different from that used for treating candidiasis and caries or the *Streptococcus mutans*.

The solutions offered are, on one hand, unilateral and segmented for each condition and, on the other hand, the active ingredients offered disregard comprehensive losses of functionality. Furthermore, there is no patented product that fully combats candidiasis, as each unique active ingredient or combination conceived to this purpose has failed in its noble and laudable goal of eliminating the disease.

The design of an effective strategy against the pernicious activity of the *Candida* species described in the various conditions mentioned requires a twofold understanding, on the one hand molecular and multitarget on the other. The random combination of natural extracts or products does not lead in any case to the achievement of positive, appropriate results applicable in clinical reality.

Labiatae are a peculiar and large family of angiosperm plants and shrubs characterized by having a square stem, opposing and decussate leaves, hermaphrodite flowers, often zigomorphs, brightly coloured, persistent calyx with firmly united corolla petals (gamopetal) whose end terminates in two parts or lips (bilabial), formed by two upper and three lower petals. As for its fruit, it is dry and consists of four nutlets. Widely known examples are rosemary, basil, lavender thyme and sage.

The existing literature contains many studies in which compounds from *Rosmarinus officinalis* (rosemary) are used against candidiasis, but always using the fraction of essential oil containing only monoterpenes: cineol, camphor, borneol, verbenone, etc., and not the polyphenolic fraction containing diterpenes and other compounds such as triterpenes and caffeic acid derivatives.

In our investigations, an extract highly and specifically enriched in diterpenes (concentration of diterpenes higher than 80%) and especially in carnosic acid (carnosic acid concentration higher than 70%) was used, with the additional presence of small proportions of carnosol and other diterpenes of similar structure.

Carnosic acid, whose structure is shown below, is a phenolic diterpene that is extracted from the leaves of the rosemary plant (*Rosmarinus officinalis*) and its antioxidant, anticancer, neuroprotective and anti-inflammatory properties as well as its preservative effect for products of various kinds, are widely known.

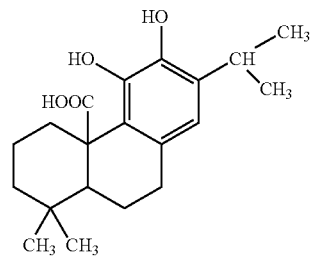 [SMILES: CC(C)c1cc2c(c(O)c1O)C1(C(=O)O)CCCC(C)(C)C1CC2]

Chemical Formula of Carnosic Acid

Currently the bibliographic information we have about the action mechanisms of this multifunctional compound is the one described below:

It does not block the release of histamine.

It reduces the release of NO, $PGE_2$, TNF-alpha triggered by PGN.

It suppresses the inflammatory response at transcription level. Src/Syk could be the target of such a response because it suppresses the kinase activity thereof.

It is a potent chemopreventive against oral carcinogenesis, probably due to its potential antilipoperoxidative and modulatory effect on carcinogen detoxification enzymes during oral DMBA-induced carcinogenesis.

At present, the use of rosemary extracts rich in diterpenes focuses exclusively on its application as antioxidant agents capable of preventing oxidation, the "rancidification" of lipids and of some proteins, however their use as "antimicrobial" agents is almost nil.

With regard to propolis, it is well known that this is a natural product produced by bees, as a result of the addition of mandibular secretions to the resins collected by these from different plants. In the hive it is used to reduce the entrances, to seal cracks and to embalm dead organisms. Its composition is very diverse as it depends on the point of collection, the plants used in its production and the particular species of bee. Its properties include: antimicrobial, antioxidant and antitumoral action.

There is evidence from a number of scientific studies on the use of propolis of a different nature in the treatment of candidiasis of different origins, however, although in these studies it is suggested that these extracts have some antifungal property, not one of them conclusively asserts an effective, reliable and safe application for the eradication of the different types of candidiasis.

In short, through the various experimental studies performed in the present invention it is demonstrated that only the combination of both extracts shows a reliable efficacy in the potential treatment of candidiasis. The results obtained show the significant molecular synergy between carnosic acid (diterpenes) and flavonoids and polyphenols present in propolis, even exceeding the usual variability in the distribution of polyphenols of the latter.

Currently, the number of products to eradicate candidiasis is growing given the prevalence of this yeast in hospital-associated infections in humans. However, despite the efforts of the scientific community in this regard, it has not been possible to obtain a truly effective product.

The number of synthetic/pharmacologic antifungals used up till now in the medical field increases year after year. However, their effectiveness is not as desirable as the current social and health problem requires. There should be mentioned some lines of products internationally marketed based on the active ingredient that they contain, such as:

Oral Route
    Fluconazole: also marketed as Fluconazole Apotex, Diflucan and Gynflu-P.
    Mycostatin: also marketed as Nystatin, Bio-Statin or Mycostatin.
    Itraconazole: also marketed as Sporanox.
    Amphotericin B.
    Ketoconazole: also marketed as Nizoral.
    Voriconazole: also marketed as Vfend.
    Nilstat: also marketed as Infestat, Korostatin, Mycostatin, Mykinac, Nysert, Nystalocal, Nystamont, Nystan, Nystatin, Nystex, Nystop.
    Candifix
    Clarithromycin.
    Terbinafine: also marketed as Lasimil.
    Micafungin.
Topical Route
    Clotrimazole: also marketed as Ginecanestén, Glynclox Lafrancol and Lotrimil.
    Miconazole: also marketed as Daktarin and Gynflu-P
    Secnidazole: also marketed as Gynflu-P.
    Clindamycin: also marketed as Gynclox Lafrancol.
    Mycostatin: also marketed as Nystatin, Bio-Statin or Mycostatin.
    Econazole.
    Fenticonazole.
    Ketoconazole: also marketed as Nizoral.
    Sertaconazole.
    Tioconazole.
    Terbinafine: also marketed as Lasimil.
Parenteral Route
    Amphotericin B.
    Voriconazole: also marketed as Vfend.
    Clarithromycin.
    Caspofungin.
    Micafungin.
Vaginal Suppositories
    Butoconazole: also marketed as Femstat.
    Clindamycin: also marketed as Gynclox Lafrancol.
    Nystatin.
    Ketoconazole: also marketed as Nizoral.

As for potential agents of natural origin, there exist anticandida compositions on the market of limited effectiveness and without a scientific basis to support their potential antifungal effects, as experimental tests have not been performed that have been conclusive in this regard. Products of this class can be found both of a probiotic nature (*Saccharomyces boulardii, Lactobacillus acidophilus*, etc.) as of a vegetable nature (grapefruit seed extract, aloe vera, garlic, etc.) resulting in heterogeneous mixtures without an established synergy, being simple "cocktails" that try to cover spectra of random and inefficient action, yielding eminently commercial products. Due to such mixtures being complex and nonspecific both in their composition and mechanisms of action, some have even included, without any synergistic basis, among their more than fifteen or twenty compounds, propolis or some labiatae plant extracts containing polyphenols of caffeic acid, but not of a diterpene nature (absence of carnosic acid and other diterpenes), thus being possible to find these products in naturopathy shops and nonspecific online selling businesses, with no medical or scientific basis. There should be mentioned examples such as "Puri-corp", "Holoprolis spray", "Candaway", "Candinorm" or "Candi clear".

Unlike the above-mentioned cases, in the present application, the standardised experimental tests that have been conducted demonstrate the effectiveness thereof, concluding that the magnitude of the resulting synergy significantly exceeds anticandidiasis products of greater impact used so far. In addition to the support of outright scientific evidence, a non-specific mixture is not used in the present application to give a "cocktail" that covers very broad fields of action to make sure that at least some of the added compounds are really effective in the desired application, but two specific compounds have been specifically selected that form the basis of the patent and its specific application.

No documents have been found in the background art describing the use of the active ingredients used herein to combat candidiasis in its various manifestations.

In the present application, the innovation that it presents in its chemical composition is of such a high degree that there is no document in the background art, in relation to the object of the present invention, that has described the use of extracts of Labiatae plants with diterpenes contained in ratios of above 80% and a concentration of carnosic acid higher than 70% combined with propolis extracts containing polyphenols at a concentration between 70 and 90% by weight.

In this application, neither rosemary essence nor carnosic acid have been used in any way for the purpose of preventing ageing, whereby the present composition is directed at treating candidiasis in all its forms whether topical or systemic, proving rigorously, scientifically and accurately our statements through the elimination of the *Candida* observed in the examples of the present application.

DESCRIPTION OF THE INVENTION

The present invention provides a synergistic composition comprising
    propolis comprising polyphenols at a concentration between 70 and 90% by weight of the propolis and
    carnosic acid,
for use in the prevention and treatment of candidiasis in humans and/or animals, hereinafter composition for use of the invention.

The invention is also defined as a method of prevention and/or treatment of candidiasis in humans and/or in animals, including the administration of a synergistic composition comprising
    propolis comprising polyphenols at a concentration between 70 and 90% by weight of the propolis and
    carnosic acid,
for use in the prevention and treatment of candidiasis in humans and/or animals.

The invention is also defined as the use of a synergistic composition comprising
    propolis comprising polyphenols at a concentration between 70 and 90% by weight of the propolis and
    carnosic acid, for the manufacture of a drug for the prevention and/or treatment of candidiasis in humans and/or animals.

Another mode for carrying out the invention is a synergistic composition consisting of:

propolis comprising polyphenols at a concentration between 70 and 90% by weight of the propolis and carnosic acid, for use in the prevention and treatment of candidiasis in humans and/or animals.

The synergistic composition for use of the invention is employed, through the administration of an effective dose, as an essential product to prevent and/or combat mucosal candidiasis in the vaginal tract, in the form of gel, cream, ointment and suppositories as well as wipes.

The synergistic composition, for use of the invention is employed, through the administration of an effective dose, as an essential product to prevent and/or combat candidiasis in cases where it appears as a very virulent pathogen, as occurs when the immune system is lowered or severely weakened, in patients undergoing intensive surgery or transplant recipients, infants, the elderly and persons subject to antitumoral therapy or prolonged antibiotic treatments; and the emergence of invasive candidiasis in persons affected with AIDS and septicemia.

The combination of propolis comprising polyphenols at a concentration between 70 and 90% by weight of the propolis and carnosic acid is also used as a bioactive ingredient in objects for pets as well as in various veterinary applications.

Another mode for carrying out the invention is the synergistic composition for use of the invention, wherein the concentration of propolis is between 20 and 80% by weight relative to the total of the synergistic composition.

Another mode for carrying out the invention is the synergistic composition for use of the invention, wherein the carnosic acid is between 10 and 60% by weight relative to the total of the synergistic composition.

Another mode for carrying out the invention is the synergistic composition for use of the invention, wherein the candidiasis is epithelial candidiasis.

The synergistic composition for use of the invention is employed, through the administration of an effective dose, as an essential product to prevent and/or eliminate epithelial candidiasis in the scalp and nails.

Another mode for carrying out the invention is the synergistic composition for use of the invention, that is selected from the group consisting of cream, gel, ointment, vaginal suppositories, sprays, tablets, powders for topical use, capsules, powder for oral suspension, ear drops, toothpaste, mouthwash, perfusion, syrup, wipes, dental thread, dental floss, toothbrush and interdental brush.

The synergistic composition for use of the invention is used as a spray (aerosol) to prevent and/or combat oral-pharyngeal and bronchitic conditions.

The synergistic composition for use of the invention is used in the form of eardrops for the prevention and/or treatment of otitis.

The synergistic composition for use of the invention is used as a basic product in the prevention and maintenance of correct oral and dental prosthesis hygiene, especially in the case of diabetes, and dental implants susceptible to developing candidiasis, through toothpaste, mouthwash and cleansing fluids.

The invention also provides a synergistic pharmaceutical and/or veterinary composition comprising:

propolis comprising polyphenols at a concentration between 70 and 90% by weight of the propolis and carnosic acid, together with pharmaceutically and/or veterinarily acceptable excipients, for use in the prevention and treatment of candidiasis in humans and/or animals, hereinafter synergistic pharmaceutical and/or veterinary composition of the invention.

In the present invention, the term "excipient" is understood as that material included in the dosage forms and is added to the active ingredients or to their combinations to enable their preparation and stability. Examples of excipients are agglutinants, fillers, disintegrants, lubricants, coatings, sweeteners, flavourings and colouring agents. More specific non-limiting examples of acceptable excipients are starch, sugar, sorbitol, xylitol, calcium phosphate, spheroids fats, talc, silica or glycerine among others.

Another mode for carrying out the invention is the synergistic pharmaceutical and/or veterinary composition of the invention, wherein the concentration of propolis is between 20 and 80% by weight relative to the total of the synergistic pharmaceutical and/or veterinary composition.

Another mode for carrying out the invention is the synergistic pharmaceutical and/or veterinary composition of the invention, wherein the concentration of carnosic acid is between 10 and 60% by weight relative to the total of the synergistic pharmaceutical and/or veterinary composition.

Another mode for carrying out the invention is a synergistic pharmaceutical and/or veterinary composition of the invention, wherein said excipients are selected from the group consisting of agglutinants, fillers, disintegrants, lubricants, coatings, sweeteners, flavouring, colouring agents, sugars, xylitol, calcium phosphate, fat spheroids, talc, polysorbate, propylene glycol, isopropyl alcohol, microcrystalline cellulose, magnesium stearate, lactose, monohydrate lactose, rice starch, maltodextrins, lauryl sodium sulfate, sorbitol, light precipitated calcium carbonate, sodium bicarbonate, sodium silicate solution, sodium saccharin, sodium carboxymethyl cellulose, light mineral oil, purified water, colloidal silica, sucrose, anhydrous colloidal silica, gum arabic, sodium citrate, anhydrous citric acid, sodium chloride, sodium hydroxide, glycerine, hydroalcohol with glyceryl polymethacrylate, eudermic surfactants, ethanol and benzalkonium chloride.

The invention also provides a synergistic food product comprising propolis comprising polyphenols at a concentration between 70 and 90% by weight of the propolis and carnosic acid, for use in the prevention and treatment of candidiasis in humans and/or animals, hereinafter synergistic food product of the invention.

The combination of propolis comprising polyphenols at a concentration between 70 and 90% by weight relative to the propolis and carnosic acid is also used as a bioactive ingredient in foods.

Another mode for carrying out the invention is the synergistic food product of the invention, selected from the group consisting of chewing gum, gumdrops, lollipops and sweets.

Another mode for carrying out the invention is the synergistic food product of the invention, wherein the concentration of propolis is between 20 and 80% by weight relative to the total of the food product.

Another mode for carrying out the invention is the synergistic food product of the invention, wherein the concentration of carnosic acid is between 10 and 60% by weight relative to the total of the food product.

BRIEF DESCRIPTION OF THE DRAWINGS

FIG. 1. Viability assay on liquid YPD medium (A) and colony formation on solid YPD medium (B) on *C. albicans* strain CAI-4 to different concentrations of carnosic acid, propolis 2 and 3. It started from a preinoculum culture incubated overnight at 28° C.; the next day refreshed in YPD medium to a D.O$_{600\ nm}$=0.3. The culture was allowed to grow to D.O$_{600\ nm}$=0.6 at 37° C., moment at which the compounds, object of the study, are added for one hour at the same temperature. Additionally, a positive control of antifungal activity with amphotericin B was included under the same conditions.

Figure 1:
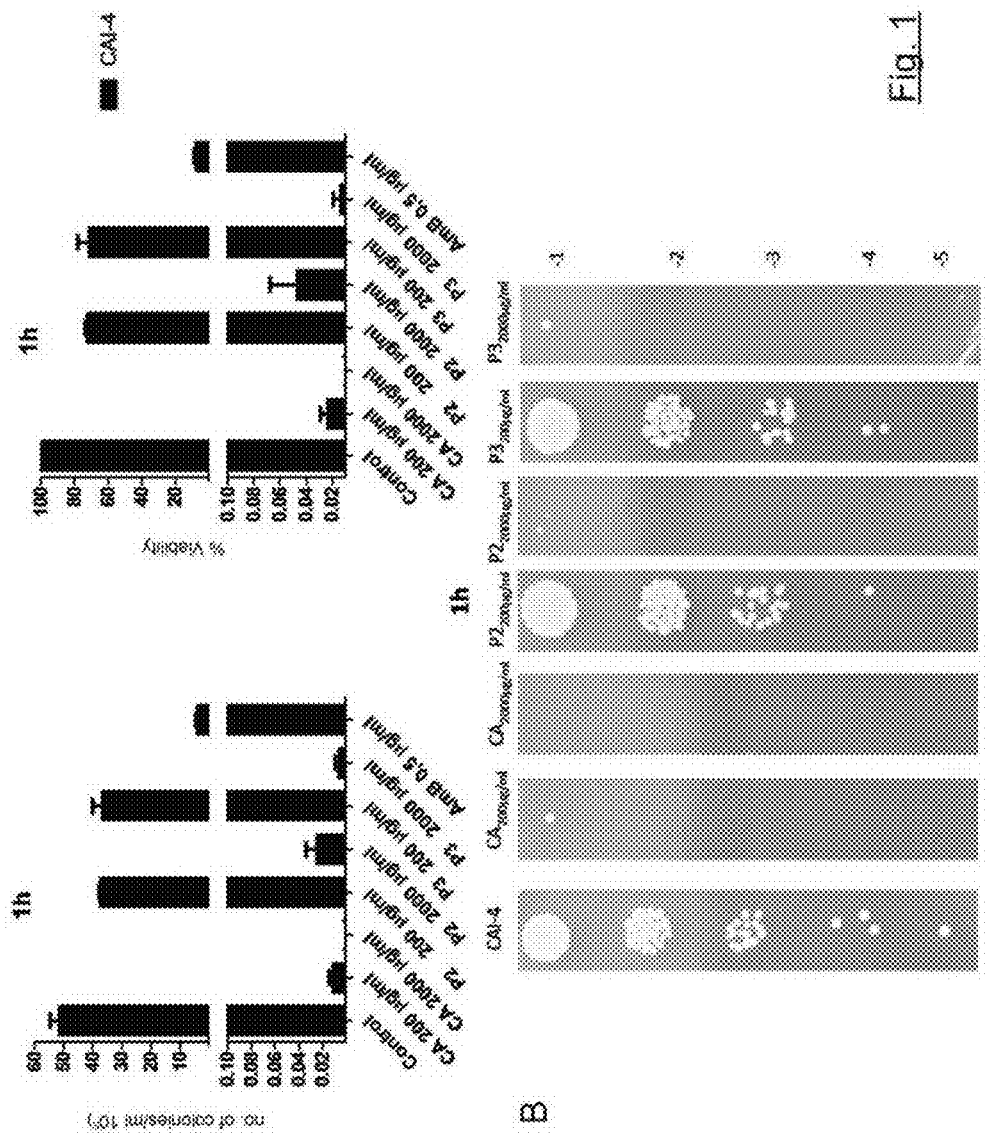
Figure 2:
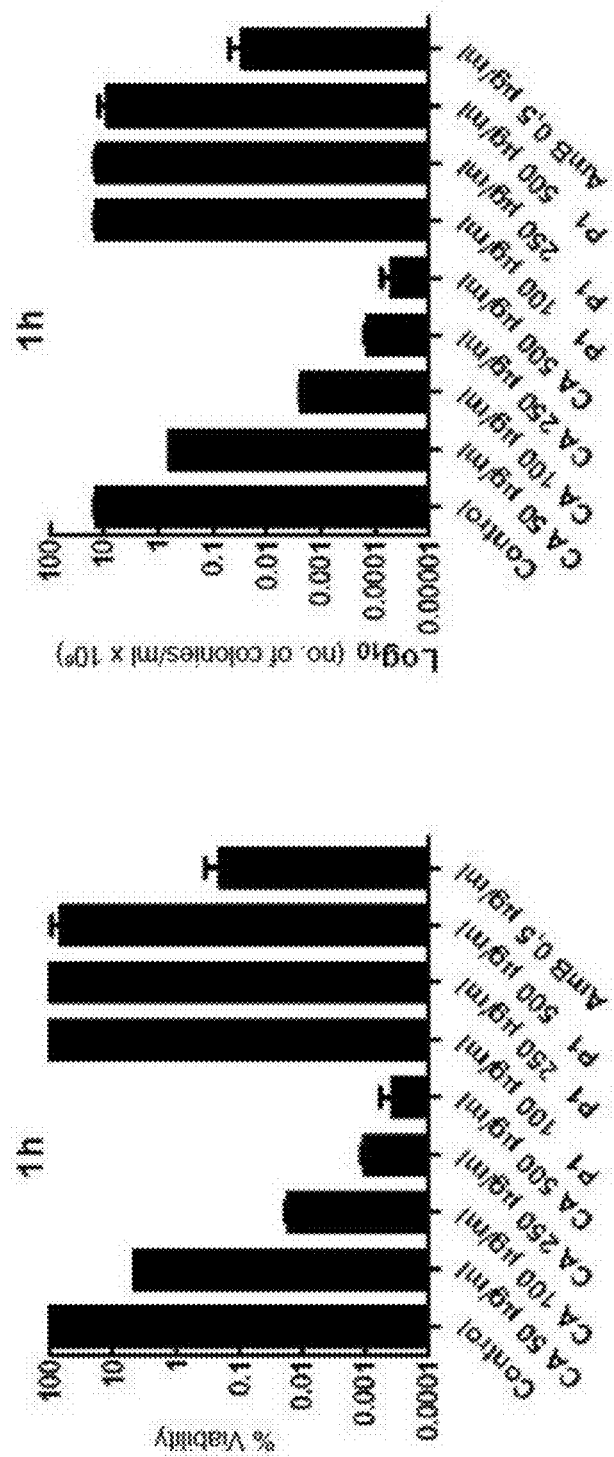

FIG. 2. Viability assay in liquid medium of the C. albicans standard strain SC5314 to different concentrations of carnosic acid and propolis 1. As a positive control Amphotericin B was used. Due to the particular behaviour of the CAI-4 strain when carrying out MICs, it was decided to use the wild strain SC5314 (ISC-4 parental), in order to validate the effect of the compounds of study on an international C. albicans reference strain. The assay followed the same procedure described in FIG. 1.

Figure 3:
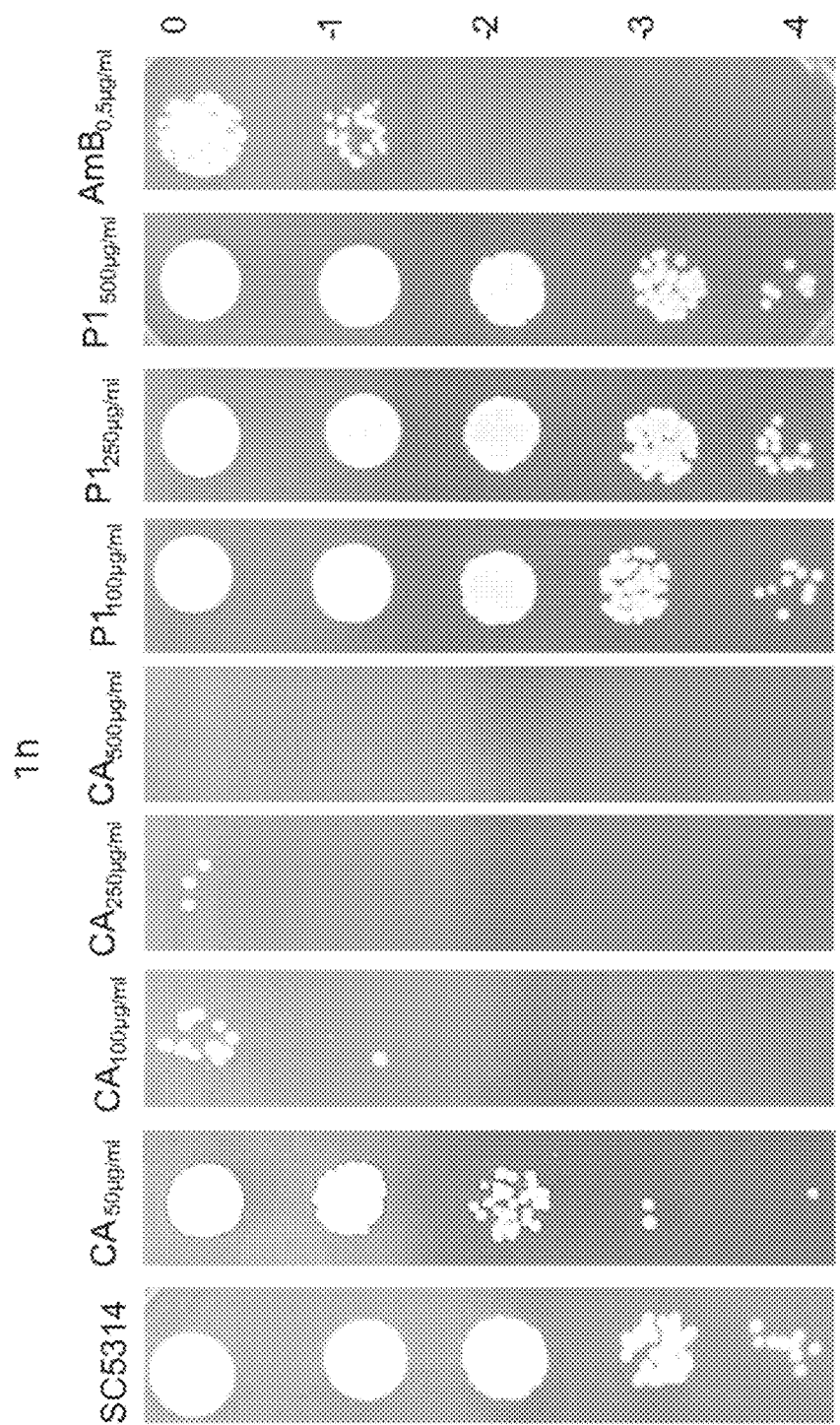

FIG. 3. Assay of macroscopic colony formation in solid YPD medium. The C. albicans standard strain SC5314 was used to the concentrations of carnosic acid and propolis 1 indicated. As a positive control Amphotericin B was used. For further details of methodology see FIG. 1.

Figure 4:
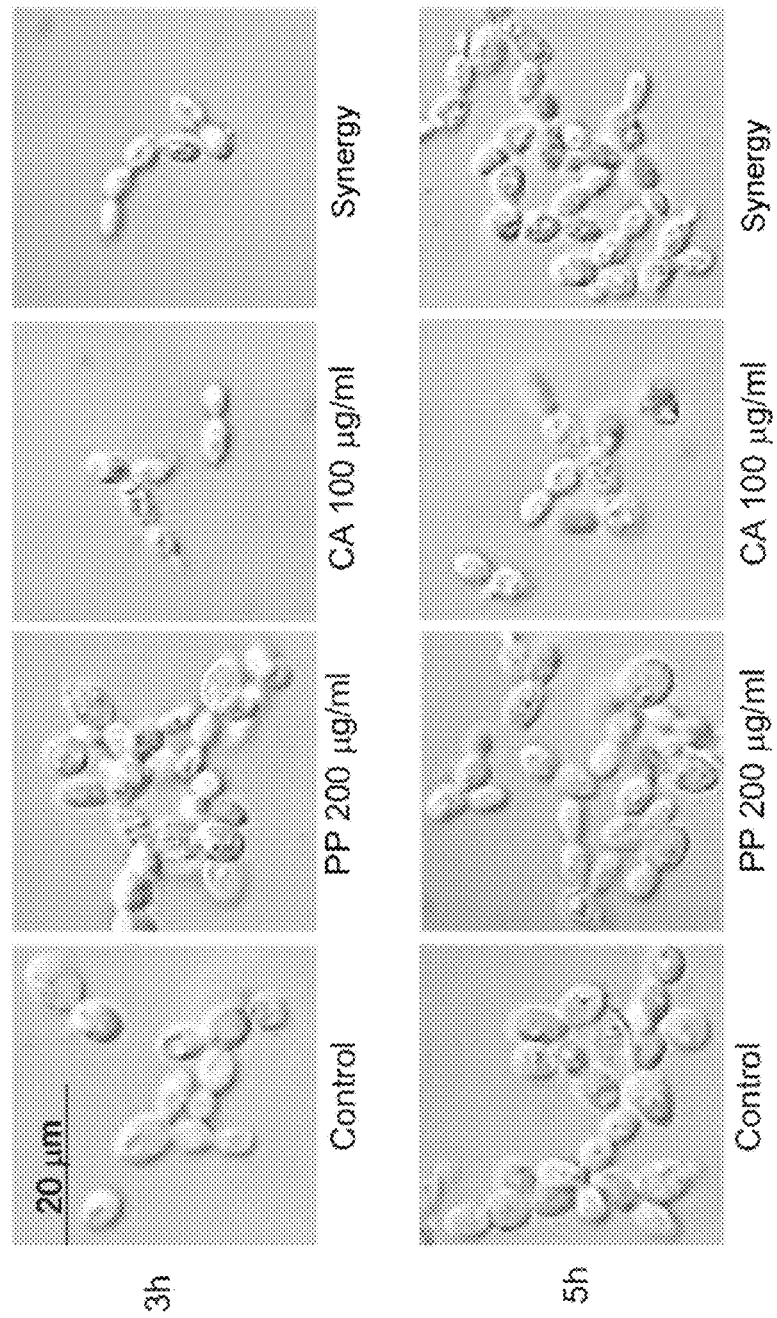

FIG. 4. Inspection of the cell morphology by optical microscopy, using the interference contrast of "Nomarsky" on C. albicans yeast (blastoconides) CAI-4, treated with: propolis 3 (200 µg/ml), carnosic acid (100 µg/ml) and the combination of both compounds. Greater granularity was observed in the samples treated with propolis in relation to the control. The presence of carnosic acid alone and its treatment in combination with propolis also caused a significant reduction in cell size, together with the aforementioned increased cellular granularity.

Figure 5:
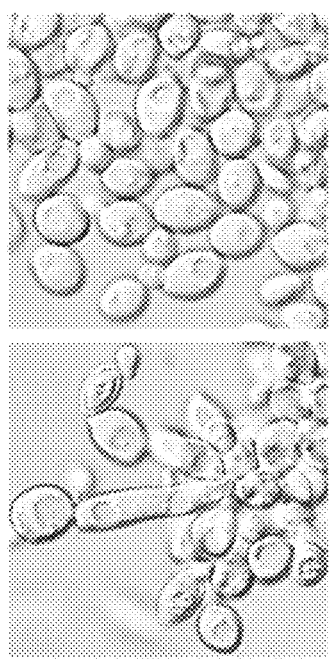
Figure 5:
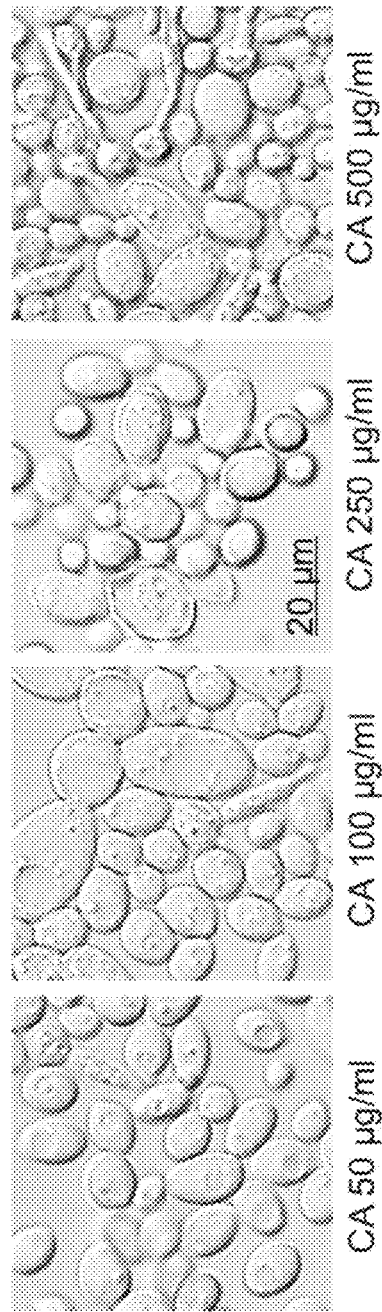

FIG. 5. Optical micrographs (100×) where it can be seen how the treatment with increasing doses of carnosic acid caused visible alterations in the cellular morphology, resulting in cells with a more swollen and deformed aspect, with increased birefringence and the apparent loss of ability to transition dimorphically to mycelial structures (hyphae). The observation under the microscope using differential Nomarsky contrast showed how cells underwent a growing swelling after treatment with 100 µg/ml of carnosic acid.

Figure 6:
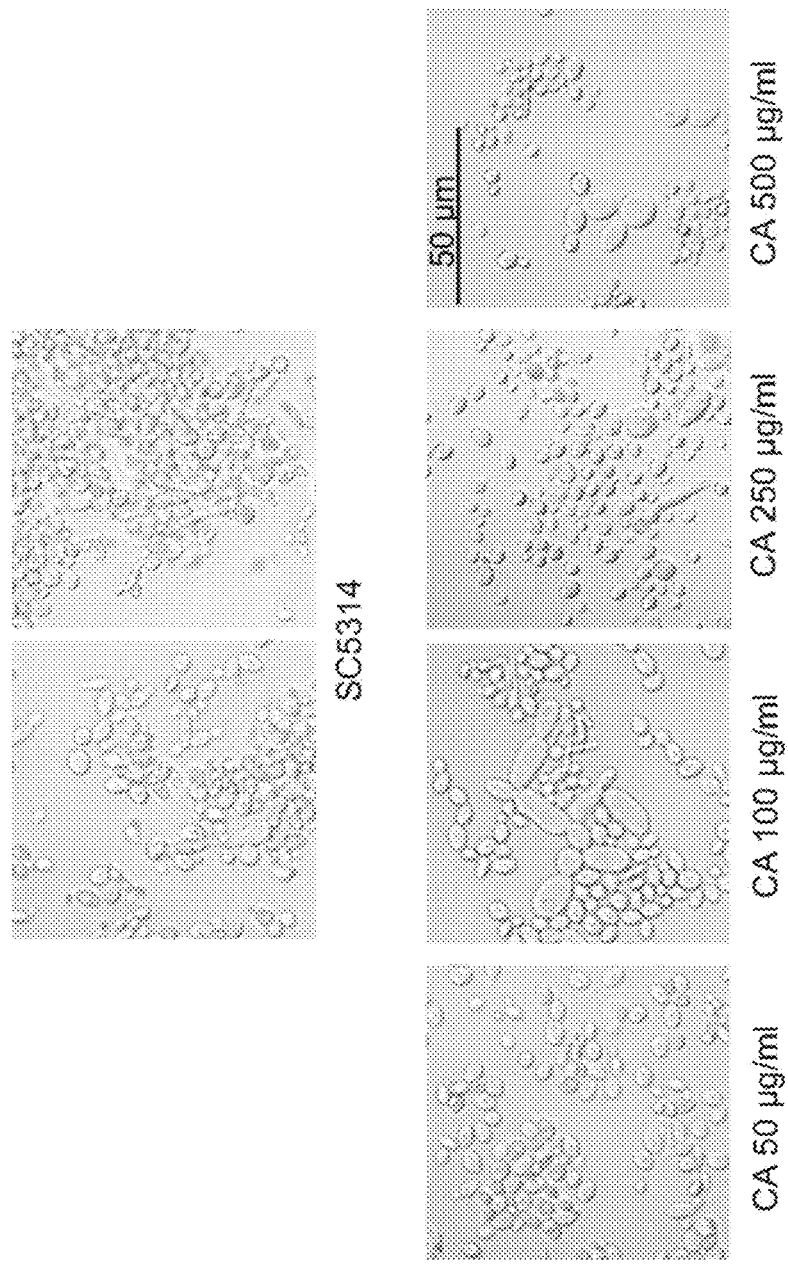

FIG. 6. Optical micrographs (40×) taken in order to provide better visual field with higher cell density, using the same cultures as in FIG. 5. The presence of swollen cells is very significant in the image, with a carnosic acid concentration of 100 µg/ml. The last photograph (500 µg/ml) shows a small number of cells, probably due to the lethal effect of carnosic acid at this concentration.

Figure 7:
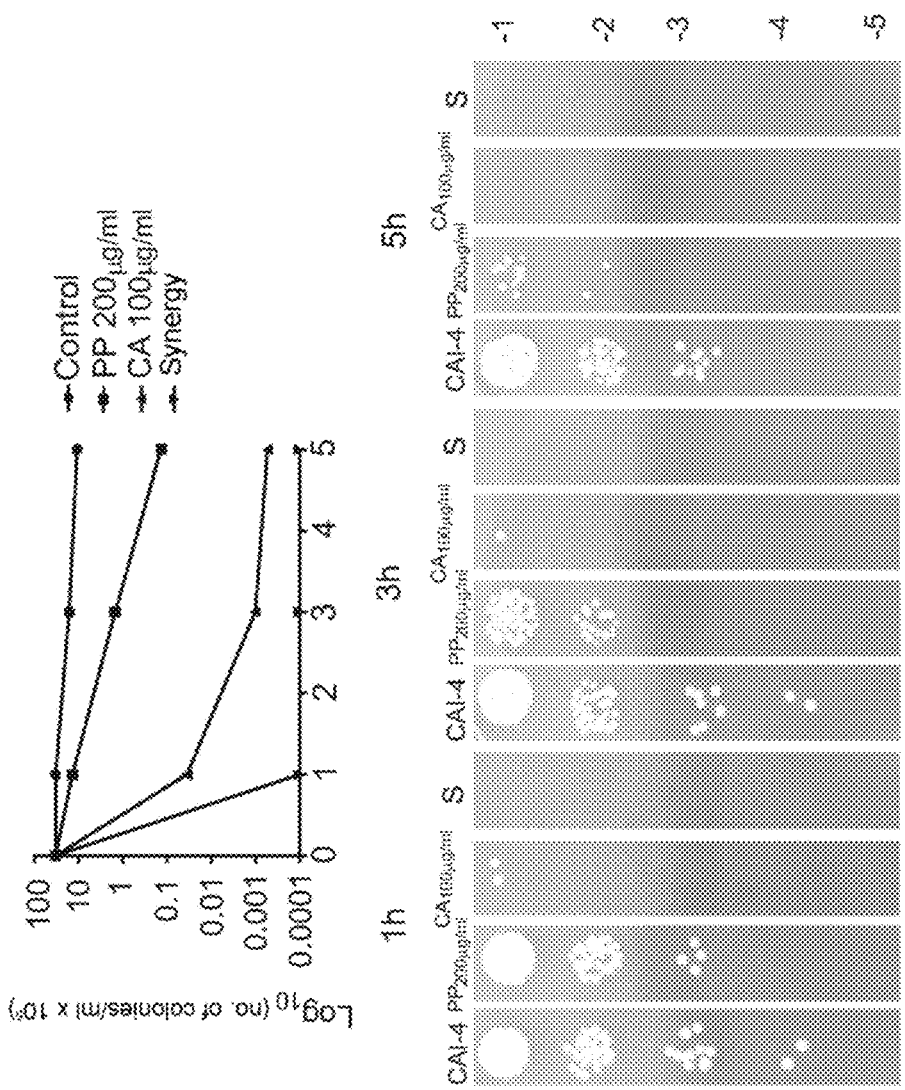

FIG. 7. Assay to measure the inhibition kinetics of CAI-4 blastoconides against certain concentrations of carnosic acid, propolis 3 and the mixture of both compounds at different exposure times. The same protocol as cited in FIG. 1 was followed, except that treatment time (one hour, three hours and five hours) with carnosic acid and propolis 3 (PP) was extended.

Figure 8:
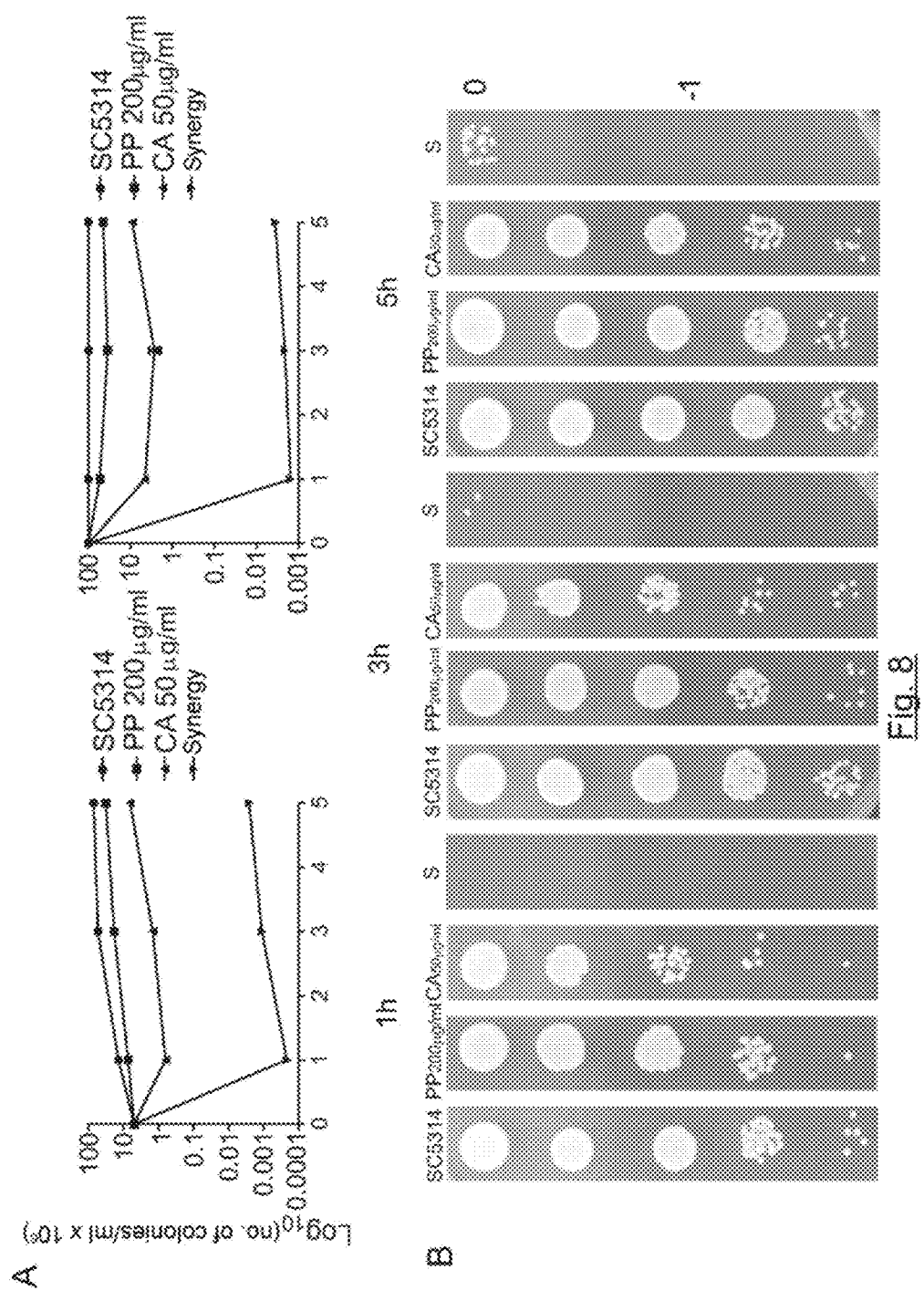

FIG. 8. (A) Measurement of the kinetic growth in the parental strain SC5314. With regard to previous assays, the following modifications were used: (i) Reduction of the concentration of carnosic acid to 50 µg/ml, maintaining that of the propolis 3 (PP) at (200 µg/ml), in order to better monitor its effect on cell viability. (ii) Inclusion of a synergistic combination of both compounds, which caused a lethal effect much higher than the result of the addition of the two individual actions. (B) Assay of colony formation on plate. The results confirm those obtained in liquid medium.

Figure 9:
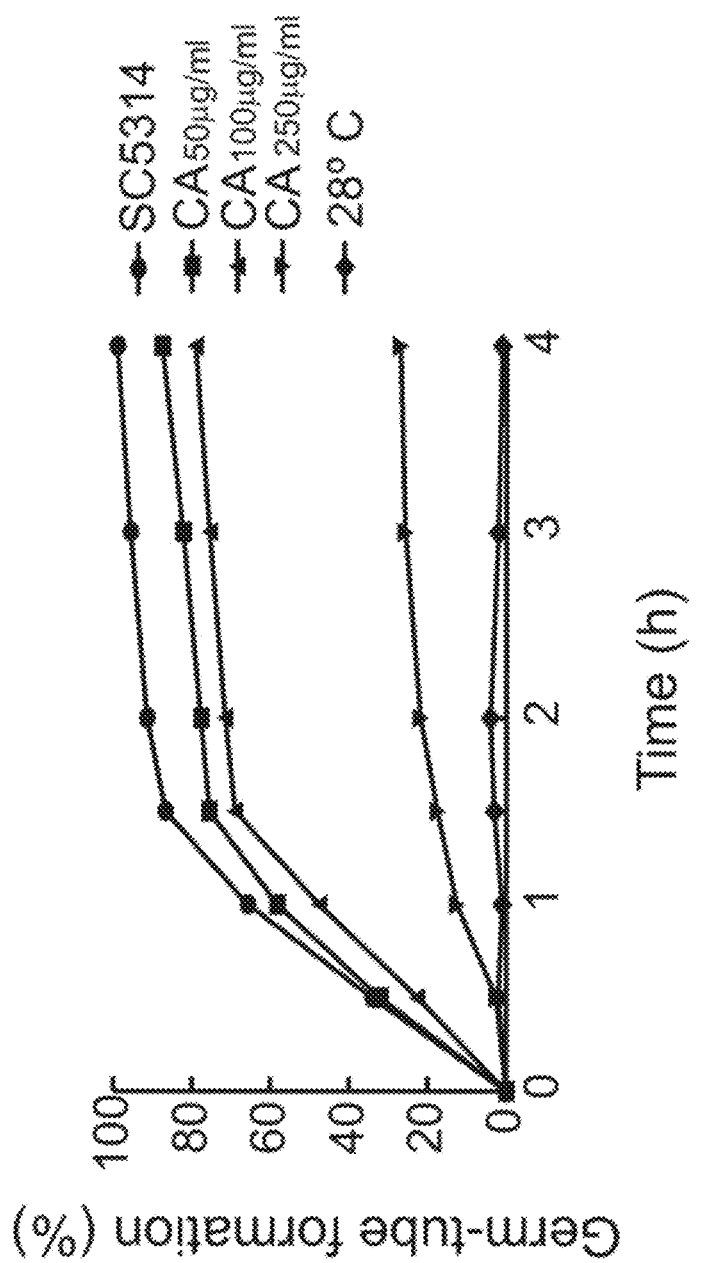

FIG. 9. Effect of the addition of carnosic acid on the percentage of yeast-hyphae dimorphic transition in C. albicans induced by human serum at 37° C. Exponential cultures of strain SC5314 were centrifuged and resuspended in fresh YPD medium preheated at 37° C. Identical samples were treated with carnosic acid at the indicated concentrations, using an untreated sample and a sample maintained at 28° C. as controls. The percentage of germ tubes emission (first stage of the formation of hyphae) was calculated by direct microscopic count with a hemocytometer.

Figure 10:
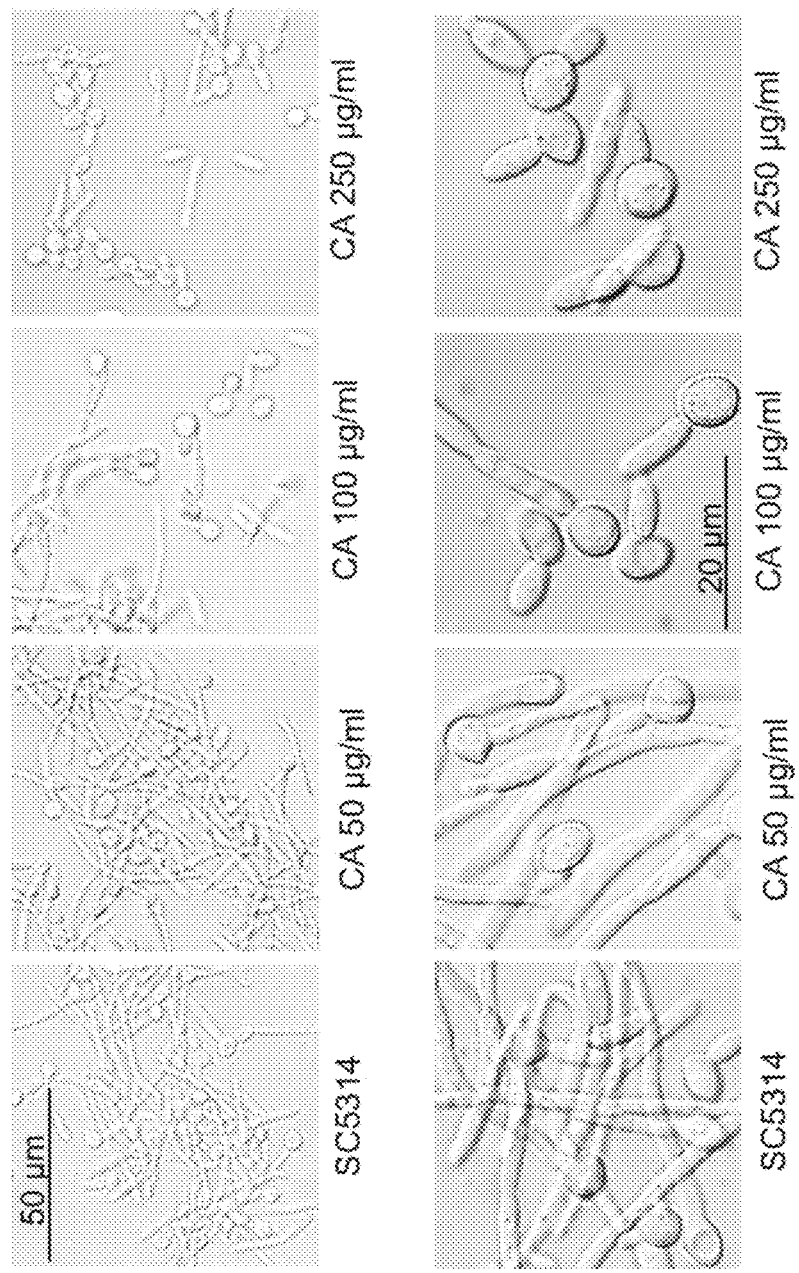

FIG. 10. Micrographs illustrating the effect of carnosic acid on the dimorphism of C. albicans. In the control assay with the lowest concentration of carnosic acid, a high percentage of filamentation (grouped hyphae forming a mycelium) which decreased proportionally with increasing dose of the latter, was observed.

Figure 11:
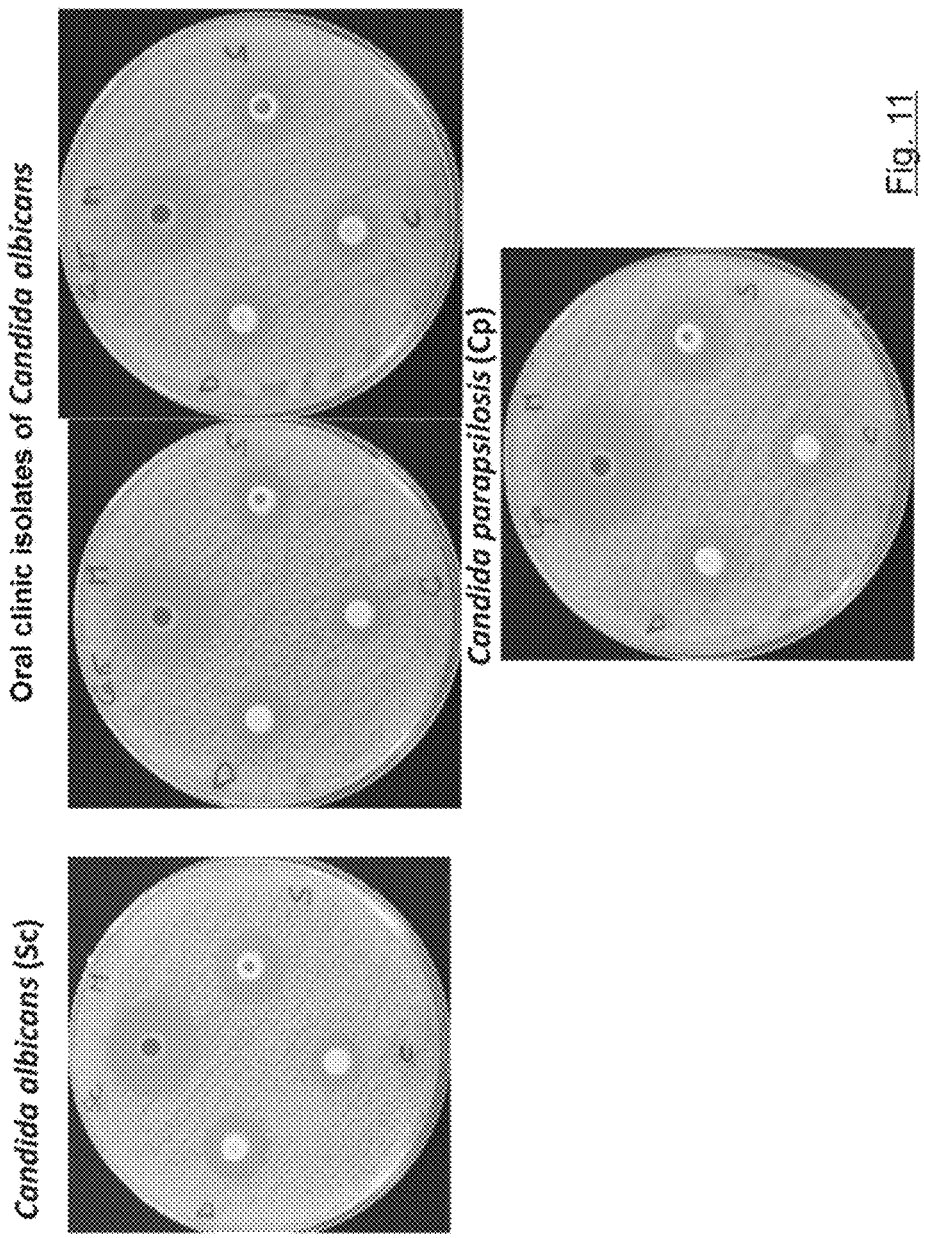

FIG. 11. Antimicrobial susceptibility profile of the antifungal activity present in commercial toothpastes of internationally renowned brands and of private labels versus toothpaste with the composition of the present application. Applied toothpastes 1:1 (1 g/1 ml) (50 µl). Toothpaste with carnosic acid and propolis (M), commercial toothpaste 1 (S), commercial toothpaste 2 (C), private label commercial toothpaste (D). For further details, see the methodological description.

Figure 12:
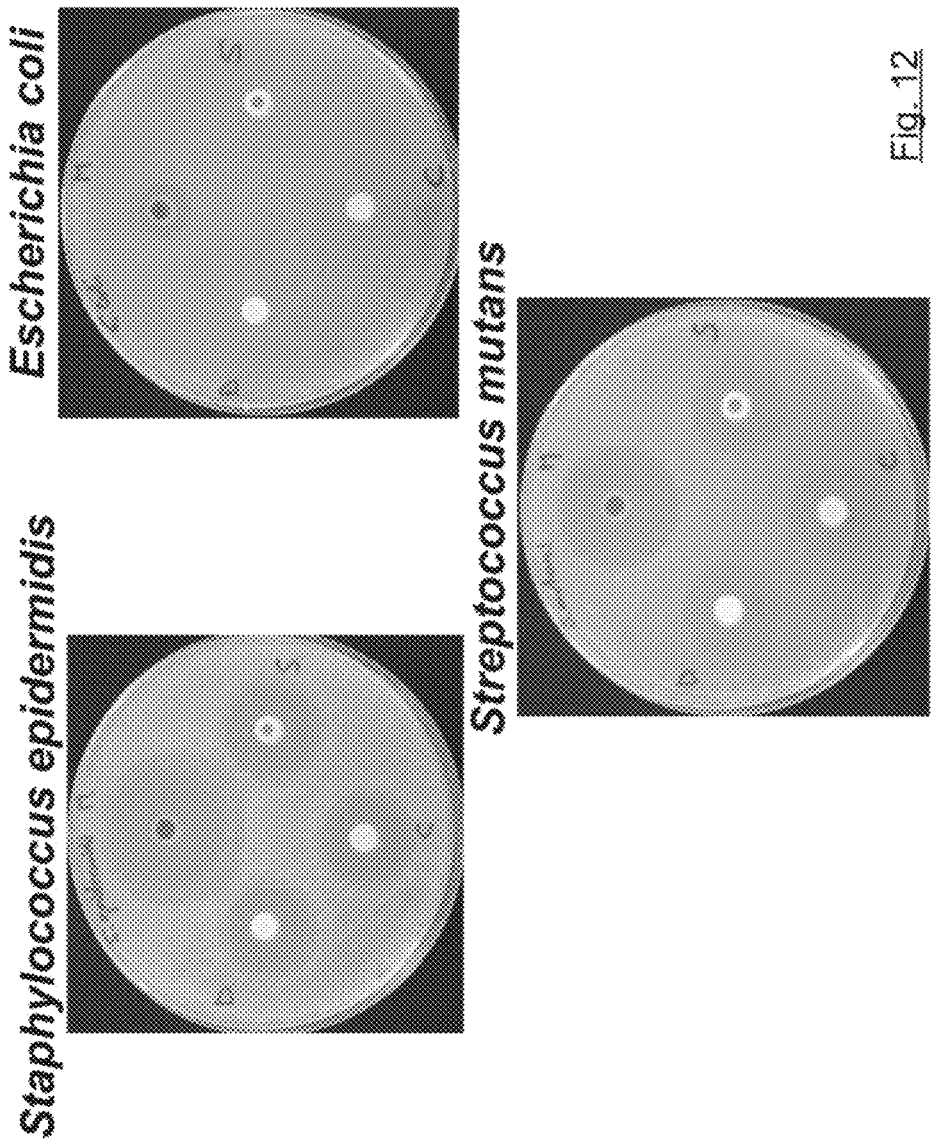

FIG. 12. Antimicrobial susceptibility profile of the antifungal activity present in commercial toothpastes of internationally renowned brands sold and of private labels versus toothpaste with the active ingredient defended in the present patent. For further details, see FIG. 11 and Materials and Methods.

PREFERRED MODES FOR CARRYING OUT THE INVENTION

Materials and Methods
Microorganisms and Extracts
The strains of C. albicans used in this study are described below, with their genotypes indicated in brackets:
Standard reference strain SC5314
Isogenic mutant CAI-4 (ura-3::imm-434/ura3::imm434)
As a natural source of carnosic acid a Labiatae plant extract was used, in this case rosemary (Rosmarinus officinalis):
Labiatae-rosemary extract with a diterpenes content higher than 80%, carnosic acid being higher than 70%.
The composition of this extract was as follows:
carnosic acid 72-80%, carnosol 2-4%, other minority diterpenes, 1-3%; water 1-2%, minerals (from the plant) 2-4%, non-active lipids (fats) 7-15%.
Three extracts of propolis were used, which were different in their concentration and distribution of polyphenols and flavonoids, analysed by HPLC by evaluating all flavonoids and polyphenolic compounds such as pinocembrin (a flavonoid characteristic of propolis) and by spectrophotometric evaluation by the universally known accepted technique named Folin-Ciocalteau:
Propolis 1, with active ingredient concentration 55-60%.
Propolis 2, with active ingredient concentration 70-75%.
Propolis 3, with active ingredient concentration 85-90%.
Cells Viability
Assays were carried out in liquid YPD medium (1% yeast extract, 2% peptone and 2% glucose) at 37° C. Initially the C. albicans strain CAI-4 was used, but as it presented growth problems during the calculation of the MIC, it was replaced by its parental (SC5314, wild type), widely used in the laboratory. The procedure consisted of applying different concentrations of carnosic acid and propolis (one hour, unless other times are indicated) on exponential cultures of *C. albicans* grown in YPD. The percentage of cell viability was determined by counting the number of viable cells in the solid YPD medium after incubation at 37° C. for 24-48 hours (FIG. 1).

According to the results presented in FIG. 1, two of the studied propolis (numbered as propolis 2 and 3) caused a significant degree of cell death on blastoconides (yeasts) CAI-4 (about 30-35%) with the lowest concentration used (200 µg/ml), being much more drastic at a dose of 2000 µg/ml. The antifungal activity of the propolis 3 is higher than propolis 2 at 2000 µg/ml. Moreover, the inhibition caused by propolis 1 was negligible (data not shown).

In turn, carnosic acid had a strong antifungal effect at concentrations of 200 y 2000 µg/ml (FIG. 1). This effect was significantly greater than that produced by the propolis. The results in liquid medium showed good correlation with the colonial growth recorded by "drops" in solid YPD (FIG. 1).

In all cases, a positive antifungal control corresponding to polyene amphotericin B (AmB) was included.

Inhibition Kinetics

As already indicated, the strain CAI-4 had growth difficulties during the MICs calculation. Consequently, it was necessary to repeat the experimental approach of FIG. 1, with a modification consisting in adding various concentrations of carnosic acid and propolis on identical aliquots of *C. albicans* SC5314 from exponential YPD liquid cultures. As shown in FIGS. 2 and 3, carnosic acid caused a significant decrease in cell viability, which was proportional to the dose used; whilst with propolis 1 no significant effects occurred, as previously discussed. The parallel determination of colony growth on solid YPD confirms the validity of these assays. Considering the group of results described in FIGS. 1, 2 and 3, it was concluded that propolis 3 sample was the most suitable for this invention.

Through all the events performed, the existence of a relatively proportional relationship is suggested between the total content of flavonoids and polyphenolic compounds present in the propolis extracts and their antifungal activity, independently from a specific distribution of said compounds (fingerprint). Accordingly, the present invention involves and includes the use of any propolis extract in its synergistic combination with carnosic acid (as described later), with the simple need to establish the ratio of both extracts in function of the concentration of bioactive compounds.

The MIC for the parental strain SC5314 of the carnosic acid was 250 µg/ml, a value identical to that previously calculated for CAI-4.

Studies on Cell Morphology

As an essential tool in understanding the effectiveness of these compounds on *C. albicans* cell viability, detailed studies on the effects of their administration on the cell morphology of this opportunistic pathogen, visualized by optical microscopy, were performed (FIGS. 4, 5 and 6). After the application of propolis 3 (FIG. 4), on the CAI-4 strain, no damage to the external appearance of the cells was observed. However, the presence of carnosic acid caused an apparent cellular reduction of size (volume) more significant after five hours of treatment, together with an increase in internal density and cytosolic cellular granularity. A more pronounced effect on both processes was observed after the synergistic addition of both compounds.

In the case of the SC5314 strain, it is clearly seen how its yeast cell morphology varies with the increasing concentration of carnosic acid applied (FIGS. 5 and 6), the cell being slightly more oval with some irregularities in its contour, probably due to osmotic changes that have resulted in the death of said cell. In said images, (FIGS. 5 and 6), the deterioration caused by the carnosic acid in the cell morphology is remarkable, causing swelling and deformation of the yeast cells (blastoconides).

Example 1. Results of Combination of Both Extracts Versus *Candida* spp. Synergy Once established the basis for evaluation of the antifungal activity of the extracts used (including their influence on cell morphology), the determination of the potential synergy between the main components was established as a basic premise of this patent. Throughout the study, extracts of rosemary and the named propolis 2 and 3 were used; although in these examples only the combination results (carnosic acid plus propolis 3) are collected due to their special and greater relevance. First of all, a preliminary evaluation with the CAI-4 strain was held, as described in FIG. 7, using predefined concentrations of both extracts: 100 µg/ml for the carnic acid and 200 µg/ml for the propolis 3.

In this first assay, the existence of the synergistic actuation between both compounds must be emphasized, inducing a very high degree of mortality, almost complete after an hour of treatment (FIG. 7), significantly higher than that recordable by the individual action of each substance (FIG. 7). Again, the extent of plate colonial growth showed concordance with the results recorded in liquid medium (FIGS. 7-9).

Then, in strain SC5314, as it is a reference lineage, new experiments simultaneously measuring the kinetics of inhibition of cell viability at sub-inhibitory concentrations of the carnosic acid (up to 50 µg/ml) and propolis 3 (200 µg/ml) were conducted together with the synergy assays between the two. The tested aliquots come from a single initial exponential culture and, therefore, the physiological state of the cells is identical.

In using the reference strain described, comparable in any laboratory in the world, the registered fungicide action was even more evident (FIGS. 8 and 9), using concentrations even lower than the MIC (50 µg/ml). Indeed, the results represented in FIGS. 8 and 9 confirm the strong antifungal action of the carnosic acid and the weaker in the case of propolis 3, considered individually. Specifically, in the synergy column (S) in FIG. 8, it can be seen that no growth is observed in one hour and also the colonial formation is virtually nil in three to five hours. However, growth is visible in the experiments with carnosic acid and propolis (individually), being comparable to the control in the dilutions 0 and −1. These data support the existence of a strong synergistic effect between the carnosic acid and propolis 3.

These assays are also complemented with the evaluation of the influence on the morphology (dimorphism) of *C. albicans*. In FIGS. 9 and 10, the effect of the carnosic acid on the dimorphic transition of the strain SC5314 of *C. albicans* was explored, given that the yeast-mycelium dimorphic transition is considered to be a factor of virulence in this opportunistic pathogen. To do this, an "overnight" culture was cooled to a low optical density (0.1) and left to grow to 0.3 at 37° C. Then the cells were treated with different concentrations of carnosic acid in YPD medium plus human serum at 10%. A serum-free culture at 28° C. was left to grow in parallel as a filamentation negative control. It can be clearly observed how the carnosic acid reduced the filamentation of *C. albicans* in a dose-dependent way. However, the most remarkable fact is the confirmation of the strong synergistic action obtained after the supplement with the two components, far superior to the result of the addition of the individual effects (FIG. 8). In principle, we must assume that both compounds are relatively stable during the exposure time (up to five hours), and that the small increase in the rate of registered viability is due, possibly, to the fraction of cells that survive the fungicide action, that was able to grow in the enriched (YPD) medium used.

The experimental data confirm the (lethal) fungicidal effect of carnosic acid together with propolis 3, over the fungistatic effect. As mentioned above, with the strain SC5314, the synergy resulting from the combination of both biocompounds is remarkably higher with regard to assays with the strain CAI-4, allowing in some cases reduction of the concentration of some of them, without harming the antifungal effect of the composition of the invention.

Example 2. Application in Oral Health: *Candida albicans* and Oral Health

According to scientific studies, some antiseptic treatments may not be sufficient alone to eradicate the organisms potentially responsible for tooth decay, especially if certain pathogenic fungi are present, therefore, the oral cavity could be considered as a fungal reservoir in general and of *Candida* in particular. Thus, for its eradication it would be necessary to prevent both the exacerbation of caries and their colonisation with *Candida*.

On the other hand, a high prevalence of *C. albicans* has been confirmed, especially in cervical cavities, which represents, regardless of the socioeconomic status of patients with tooth decay, the most common opportunistic fungal species followed by *C. tropical, C. krusei* and *C. parapsilosis*.

In assays conducted with different widely used and internationally accepted commercial toothpastes, versus different infectious microorganisms such as: *Candida albicans, Candida parapsilosis, Escherichia coli, Streptococcus mutans* and *Staphylococcus epidermidis*, it is observed that the effectiveness of these in relation to the toothpaste formulated in accordance with the composition of the present application is significantly less, not only against species of *Candida* (including clinical isolates) as shown in FIG. 11, but also compared to other mentioned pathogens (FIG. 12).

Table 1 contains a comparative analysis of the effectiveness of each one of the toothpastes used.

TABLE 1

| | 6 mm punch | | |
| --- | --- | --- | --- |
| Strains 50 µl | Sample | Commercial toothpaste 1 | Commercial toothpaste 2 | Private label commercial toothpaste |
| Inhibition halos diameter (mm) | | | |
| C. albicans | 22 | 14 | 12 | 12 |
| C. parapsilosis | 28 | 18 | 10 | 10 |
| Ca15 | 22 | 12 | 10 | 12 |
| Ca25 | 20 | 12 | 10 | 10 |
| S. epidermidis | 30 | 20 | 18 | 18 |
| E. coli | 10 | — | — | — |
| S. mutans | 30 | 20 | 18 | 20 |

Table 1. Diameter of the halos of inhibition (in millimeters) produced by different commercial toothpastes versus various pathogenic microorganisms. A diameter markedly greater can be appreciated in the case of the toothpaste formulated with ingredients defended in the present patent against all the microorganisms, emphasising once more its greater antimicrobial power.

On the other hand, if the growth of the micro-organisms is promoted before the application of the toothpaste in order to more closely emulate its real application, allowing that they have the opportunity to achieve their potential pathogenic threshold, the antimicrobial effects observed are equally notable in the toothpaste that contains active ingredients described in the patent when compared with the rest (Tables 2 and 3).

TABLE 2

| | 6 mm punch | |
| --- | --- | --- |
| Strains 50 µl | Sample | Commercial toothpaste 1 | Commercial toothpaste 2 |
| Inhibition halos diameter (mm) | | |
| C. albicans | 22 | 14 | 10 |
| C. parapsilosis | 24 | 10 | — |
| Ca15 | 26 | 14 | 10 |
| Ca25 | 24 | 12 | 4 |
| S. epidermidis | 28 | 18 | 16 |
| E. coli | 28 | 12 | 8 |
| S. mutans (BHI) | 28 | 22 | 18 |

Table 2. Diameter of the halos of inhibition (in millimeters) produced by different commercial toothpastes versus various pathogenic microorganisms. In this assay, the microbial growth (five hours) by preincubation of the plates at 37° C. was allowed before adding the compounds, so they could reach more pathogenic potential. A diameter markedly greater can be appreciated in the case of the toothpaste formulated with ingredients defended in the present patent against all the microorganisms, emphasising once more its greater antimicrobial power.

TABLE 3

| | 6 mm punch | |
| --- | --- | --- |
| Strains 50 µl | Sample | Commercial toothpaste 1 | Commercial toothpaste 2 |
| Inhibition halos diameter (mm) | | |
| C. albicans | 14 | — | — |
| C. parapsilosis | 18 | — | — |
| Ca15 | 10 | — | — |
| Ca25 | 12 | — | — |
| S. epidermidis | — | — | — |
| E. coli | 12 | — | — |
| S. mutans (BHI) | — | — | — |

Table 3. Diameter of the halos of inhibition (in millimeters) produced by different commercial toothpastes versus various pathogenic microorganisms. In this case, prior growth of the cultures was allowed (twelve hours of pre-incubation) so that they attained more pathogenic potential. As shown, only the toothpaste formulated with the ingredients defended in the present patent produces significant inhibition halos, while no inhibition halos were observed with the other commercial toothpastes.

Finally, experiments have been conducted with oral clinical isolates of *C. albicans* in order to take the experimental part to the most realistic extremes, the conclusions being identical to the above (11 and Tables 1-3).

Example 3. Examples of Form of Application, Vehicles and Systems for Application-Dosage Applicability Considering the many possibilities and needs of application of this synergistic combination, different dosage forms and systems thereof are included. The application of this aforementioned formula requires different applications:

For oral health, toothpaste represents a mechanism with simultaneous multifactorial action against degenerations and losses of function also of multifactorial origin, covering both candidiasis, avoiding dental caries and gingivitis, as well as the standardization of the saliva and oral flora.

In infection of women's private parts, the application would take place by means of wipes, as the mouth and the vagina have the same epithelial composition of lysozyme and mucous membranes. In turn, in systemic candidiasis, the application would be through the form of a syrup or an injection.

To establish the correct applicability of the synergistic composition of the present application, all adequacy tests of said formulation with the excipients described below were performed, the same resulting correct in all cases included:

Cream
1. Propylene glycol
2. Polysorbate

Spray
1. Propylene glycol
2. Isopropyl alcohol

Tablets
1. Microcrystalline cellulose
2. Magnesium stearate
3. Lactose

Topical use Powders
1. Rice starch
2. Maltodextrins

Capsules
1. Lactose or monohydrate lactose
2. Microcrystalline cellulose
3. Corn starch
4. Magnesium stearate
5. Lauryl sodium sulphate
6. Colloidal silica dioxide Powder for Oral Suspension
1. Sucrose
2. Anhydrous colloidal silica
3. Gum arabic
4. Sodium citrate
5. Anhydrous citric acid Perfusion
1. Sodium chloride
2. Sodium hydroxide to adjust the pH Syrup
1. Glycerine Wipes
1. Hydroalcohol with glyceryl polymethacrylate
2. Eudermic surfactants
3. Ethanol
4. Propylene glycol
5. Benzalkonium chloride

The invention claimed is:

1. A synergistic composition comprising:
propolis comprising polyphenols at a concentration between 70 and 90% by weight of the propolis and carnosic acid,
for use in the prevention and treatment of candidiasis in humans and/or animals.

2. Synergistic composition for use according to claim 1, wherein the candidiasis is epithelial candidiasis.

3. Synergistic composition for use according to claim 1, wherein the concentration of propolis is between 20 and 80% by weight relative to the total of the synergistic composition.

4. Synergistic composition for use according to 1, wherein the concentration of carnosic acid is between 10 and 60% by weight relative to the total of the synergistic composition.

5. Synergistic composition for use according to claim 1, wherein the synergistic composition is provided in the form selected from the group consisting of cream, gel, ointment, vaginal suppositories, sprays, tablets, powders for topical use, capsules, powder for oral suspension, ear drops, toothpaste, mouthwash, perfusion, syrup, wipes, dental thread, dental floss, toothbrush and interdental brush.

6. Synergistic pharmaceutical and/or veterinary composition comprising:
propolis comprising polyphenols at a concentration between 70 and 90% by weight of the propolis and carnosic acid,
together with pharmaceutically and/or veterinarily acceptable excipients, for use in the prevention and treatment of candidiasis in humans and/or animals.

7. Synergistic pharmaceutical and/or veterinary composition for use according to claim 6, wherein the concentration of propolis is between 20 and 80% by weight relative to the total of the synergistic pharmaceutical and/or veterinary composition.

8. Synergistic pharmaceutical and/or veterinary composition for use according to claim 6, wherein the concentration of carnosic acid is between 10 and 60% by weight relative to the total of the synergistic pharmaceutical and/or veterinary composition.

9. Synergistic pharmaceutical and/or veterinary composition for use according to claim 6, wherein said excipients are selected from the group consisting of agglutinants, fillers, disintegrants, lubricants, coatings, sweeteners, flavouring, colouring agents, sugars, xylitol, calcium phosphate, fat spheroids, talc, polysorbate, propylene glycol, isopropyl alcohol, microcrystalline cellulose, magnesium stearate, lactose, monohydrate lactose, rice starch, maltodextrins, lauryl sodium sulfate, sorbitol, light precipitated calcium carbonate, sodium bicarbonate, sodium silicate solution, sodium saccharin, sodium carboxymethyl cellulose, light mineral oil, purified water, colloidal silica, sucrose, anhydrous colloidal silica, gum arabic, sodium citrate, anhydrous citric acid, sodium chloride, sodium hydroxide, glycerine, hydroalcoholic with glyceryl polymethacrylate, eudermic surfactants, ethanol and benzalkonium chloride.

10. Synergistic food product comprising
propolis comprising polyphenols at a concentration between 70 and 90% by weight of the propolis and carnosic acid,
for use in the prevention and treatment of candidiasis in humans and/or animals.

11. Synergistic food product according to claim 10, wherein the food product is provided in the form selected from the group consisting of chewing gum, gumdrops, lollipops and sweets.

12. Synergistic food product according to claim 10, wherein the concentration of propolis is between 20 and 80% by weight relative to the total of the food product.

13. Synergistic food product according to claim 10, wherein the concentration of carnosic acid is between 10 and 60% by weight relative to the total of the food product.

14. A method for treating candidiasis in humans and/or animals comprising using the synergistic composition of claim 1.

15. The method according to claim 14, wherein the candidiasis is epithelial candidiasis.

16. The method according to claim 14, wherein the concentration of propolis is between 20 and 80% by weight relative to the total of the synergistic composition.

17. The method according to claim 14, wherein the concentration of the carnosic acid is between 10 and % by weight relative to the total of the synergistic composition.

18. A method for treating candidiasis in humans and/or animals comprising using the synergistic pharmaceutical and/or veterinary composition according to claim 6.

19. The method according to claim 18, wherein the concentration of propolis is between 20 and 80% by weight relative to the total of the synergistic pharmaceutical and/or veterinary composition.

20. The method according to claim 18, wherein the concentration of carnosic acid is between 10 and 60% by weight relative to the total of the synergistic pharmaceutical and/or veterinary composition.

\* \* \* \* \*